(12) United States Patent
Hutton et al.

(10) Patent No.: US 6,203,564 B1
(45) Date of Patent: Mar. 20, 2001

(54) BRAIDED POLYESTER SUTURE AND IMPLANTABLE MEDICAL DEVICE

(75) Inventors: Jeffrey D. Hutton, Southbury; Barry L. Dumican, Newton, both of CT (US)

(73) Assignee: United States Surgical, Norwalk, CT (US)

( * ) Notice: Subject to any disclaimer, the term of this patent is extended or adjusted under 35 U.S.C. 154(b) by 0 days.

(21) Appl. No.: 09/030,868

(22) Filed: Feb. 26, 1998

(51) Int. Cl.[7] .................................................. A61B 17/04
(52) U.S. Cl. ............................................ 606/228; 606/230
(58) Field of Search .................... 606/228, 229, 606/230

(56) References Cited

U.S. PATENT DOCUMENTS

| | | | |
|---|---|---|---|
| 2,465,319 | 3/1949 | Whinfield et al. | 260/75 |
| 3,322,125 | 5/1967 | Kurtz | 128/335.5 |
| 4,149,277 | 4/1979 | Bokros | 3/1 |
| 4,470,941 | 9/1984 | Kurtz | 264/136 |
| 4,510,934 | 4/1985 | Batra | 128/335.5 |
| 4,959,069 | 9/1990 | Brennan et al. | 606/228 |
| 4,983,180 | 1/1991 | Kawai et al. | 606/230 |
| 5,019,093 | 5/1991 | Kaplan et al. | 606/228 |
| 5,059,213 | 10/1991 | Chesterfield et al. | 606/228 |
| 5,306,289 | 4/1994 | Kaplan et al. | 606/228 |
| 5,318,575 | 6/1994 | Chesterfield et al. | 606/151 |
| 5,456,697 | 10/1995 | Chesterfield et al. | 606/228 |

FOREIGN PATENT DOCUMENTS

| | | |
|---|---|---|
| 2108603 | 4/1994 | (CA) . |
| 1337498 | 11/1995 | (CA) . |
| 2181957 | 1/1997 | (CA) . |
| 759305 | 2/1997 | (EP) . |

OTHER PUBLICATIONS

Product Brochure for Ethicon Excel™ Polyester suture, copyright by Ethicon, Inc. 1995.

*Primary Examiner*—Gary Jackson

(57) ABSTRACT

A braided polyester suture made from polyester yarn filaments having a tenacity of from about 7 to about 11 g/denier, a percent elongation to break of less than about 30 percent and the polymer from which the filaments are made has an intrinsic viscosity greater than about 0.95. The invention also provides an implantable medical device constructed from yarn filaments having these properties.

6 Claims, 2 Drawing Sheets

BRAIDED POLYESTER SUTURE AND IMPLANTABLE MEDICAL DEVICE

BACKGROUND OF THE INVENTION

1. Field of the Invention

This invention relates to a braided polyester suture made from high-tenacity polyester yarn filaments.

2. Related Background Art

Braided sutures are well known in the art as disclosed, for example in U.S. Pat. No. 5,019,093. Various natural and artificial polymeric materials have been used in manufacture of braided sutures, including surgical gut, silk, cotton, polyolefins, polyamides, polyglycolic acid and polyesters. Braided polyester sutures are useful in applications where a strong, nonabsorbable suture is needed to permanently repair tissue. They are frequently used in cardiovascular surgery, as well as in ophthalmic and neurological procedures. Examples of commercial braided polyester sutures are ETHIBOND EXCEL®, manufactured by Ethicon, Inc., TICRON® manufactured by Sherwood-Davis & Geck and TEVDEK® manufactured by Deknatel.

The surface roughness of braided sutures is of great importance to surgeons. Excessive roughness affects the knot-tying and knot-holding properties of the suture, causing an uneven movement known as "chattering." This characteristic increases the difficulty of accurately placing knots. In addition, the uneven force exerted on the suture during tying may lead to increased suture breakage. Typically, sutures are coated with a lubricating material, e.g., polybutilate, to improve the handling characteristics of the sutures.

In addition, conventional polyethylene terephthalate (PET) sutures can exhibit reduced tensile strength and have a tendency to fray. This also leads to increased suture breakage during tying of surgeon's knots.

U.S. Pat. No. 5,318,575 discloses use of high-tenacity, low-elongation fibers to produce a reinforced band for attaching tissue or bone. However, the high-tenacity, low-elongation fibers are made from polyethylene of extremely high molecular weight, with other materials being used only as filler yarns. No suggestion is made that high-tenacity polyester fibers would be suitable for use in surgical repair products.

SUMMARY OF THE INVENTION

It is an object of this invention to provide a braided polyester suture exhibiting reduced surface roughness, high tensile strength and a reduced tendency to fray.

These and other objects and advantages are achieved by a braided polyester suture produced from a polymer having an intrinsic viscosity greater than about 0.95 and formed from yarn filaments having a tenacity of from about 7 to about 11 g/denier and a percent elongation to break of less than 30 percent.

The invention is further directed to an implantable medical device produced from a polymer having an intrinsic viscosity greater than about 0.95 and formed from yarn filaments having a tenacity of from about 7 to about 11 g/denier and a percent elongation to break of less than about 30 percent.

DETAILED DESCRIPTION OF THE INVENTION

Figure 1:
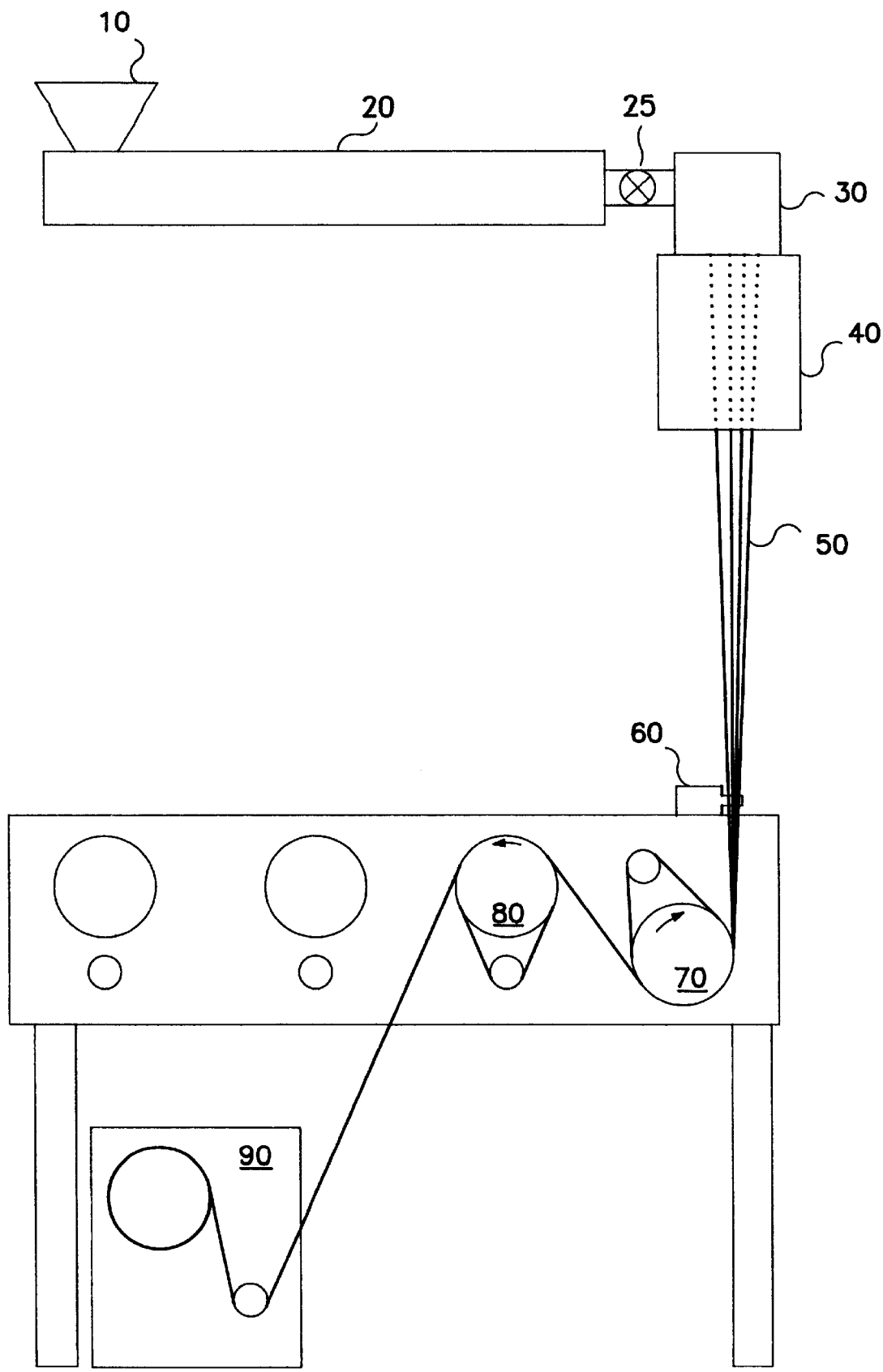
FIG. 1 is a plan view of a system for extruding polyester yarn from bulk resin.

The improved braided polyester sutures of this invention are manufactured from polyester yarn filaments produced from polymers having an intrinsic viscosity greater than about 0.95 and having a tenacity from about 7 to about 11 g/denier and a percent elongation to break of less than about 30 percent.

Preferably, the polyester employed in this invention is polyethylene terephthalate (PET). If desired, bulk resin in the form of granules, chips or pellets of a suitable PET are made into yarn filaments via a conventional extrusion process. Bulk PET with suitable properties may be obtained commercially from, for example, Shell Chemical Co., Apple Grove, W.V. distributed under the designation Cleartuf EB 1040 and Traytuf 106C and DSM Engineering Plastics, Evansville, Ind. under the designation Arnite A06 100.

Alternatively, polyester yarn with suitable properties may be obtained commercially from, for example, Hoechst Celanese under the trade name Trevira® High Tenacity type 712 or 787. The intrinsic viscosity of such yarn samples is from 1.04 to 1.07.

Preferably, the tenacity of the yarn filaments is from about 7.5 to about 10.5 g/denier, the percent elongation to break is less than about 25 percent and the polymers from which the fibers are made have an intrinsic viscosity greater than about 0.95 but no greater than about 1.1.

Most preferably, the tenacity of the yarn filaments is from about 8 to about 10 g/denier, the percent elongation to break is less than about 20 percent and the polymers from which the fibers are made have an intrinsic viscosity greater than about 0.95 but no greater than about 1.1.

The polyester yarns are made from filaments having a denier in the range from about 0.2 to about 6, preferably from about 1.2 to about 3.4, most preferably from about 1.4 to about 3.1. The polyester filaments are extruded as yarns having a denier in the range from about 20 to about 500, preferably from about 20 to about 350. The yarns are generally either conventionally twisted or entangled prior to braiding.

In one embodiment twisted PET yarns can be braided into sutures using conventional braid constructions having a sheath and optionally a core. Typical braid constructions are disclosed in U.S. Pat. No. 5,019,093, issued May 28, 1991, the disclosure of which is incorporated herein by reference. Preferred braid constructions have the parameters recited in Table 1 as follows:

TABLE 1

Preferred Braid Constructions

| Suture Size | No. of Sleeve Yarns | Sleeve Yarns (denier/filament) | Core Yarn (denier/filament) | Picks/Inch |
|---|---|---|---|---|
| 5 | 16 | 250/50 | 1000/200 | 52 |
| 2 | 16 | 140/68 | 840/408 | 57 |
| 1 | 12 | 140/68 | 630/306 | 52 |
| 0 | 12 | 100/34 | 300/102 | 42 |
| 2-0 | 8 | 140/68 | None | 39 |
| 3-0 | 8 | 80/16 | None | 39 |
| 4-0 | 4 | 70/34 | None | 39 |
|  | 4 | 40/8 |  |  |
| 5-0 | 8 | 30/20 | None | 33 |

TABLE 1-continued

Preferred Braid Constructions

| Suture Size | No. of Sleeve Yarns | Sleeve Yarns (denier/ filament) | Core Yarn (denier/ filament) | Picks/ Inch |
| --- | --- | --- | --- | --- |
| 6-0 | 4 | 30/20 | None | 32 |
|  | 4 | 20/10 |  |  |
| 7-0 | 3 | 20/10 | None | 67 |

After the braids have been assembled, they are preferably stretched in the presence of heat. Preferably, the temperature range for such stretching is from about 150° C. to about 250° C. Typically, length of the braided sutures increases by about 6% to about 33% of their original length.

The surface of the stretched braids can sometimes be unduly smooth after such treatment. An unduly smooth suture surface can make it difficult to grasp the suture and tie a desired knot. Also, stretching can greatly stiffen the braid imparting undesirable handling properties to the suture. In order to allow better control of the suture during tying it is preferred to conduct additional processing of the suture to provide appropriate surface roughness and lessen fiber stiffness to allow the surgeon to have better feel of the suture and permit easier knotting.

To further enhance the feel of the suture, the stretched braid may be surface-etched to break any adhesions present on the braid surface and to soften the braid. Such etching is conducted by applying a reactive compound such as sodium hydroxide or the like to the surface of the braid. To further control the feel of the suture surface, the braid can be passed under a matte roller or the like. The surface etching and matte roller treatments can further improve the surface feel of the braid to facilitate knot tying Optionally, the braided polyester sutures are treated with a coating material to impart improved handling to the treated braid. The preferred coating material is silastic rubber.

The braid is then formed into a suture by attaching a needle, packaging the product and then sterilizing with ionizing radiation, ethylene oxide or the like.

The filaments in the final suture product may have a molecular weight less than the molecular weight of the original polymer. It is believed that the sterilizing treatment, heating and/or stretching treatments conducted during processing of the filaments into a suture may break polymer chains and reduce molecular weight.

The improved sutures of this invention, as compared to commercially available sutures, have significantly improved tensile strength.

In another embodiment of this invention, the polyester yarns are used in providing an implantable medical device. Examples of such a device is a mesh, a graft, a ligament replacement and a tendon replacement. A mesh, or net formed from polyester yarns is typically used in surgical repair of hernias. The enhanced tenacity of the polyester yarns of this invention provides the mesh with superior strength. A graft is a knitted or woven tubular article used in replacement of blood vessels. The enhanced tenacity of the polyester yarns of this invention allows construction of a graft with thinner walls and greater flexibility. Ligament and tendon replacements comprise multiple strands of polyester yarns that have been braided, for which the yarns of the present invention provide superior strength.

In a further embodiment of the invention a braided suture is formed from yarn filaments having a weight average molecular weight of greater than 35,000, a tenacity of greater than about 6 grams/denier, an elongation to break less than about 35% and a boiling water shrinkage from about 0.5 to about 2.0%. In this embodiment the filaments have a weight average molecular weight preferably greater than 40,000 and, most preferably, from about 42,000 to 45,000. The tenacity of the filaments is preferably greater than 7 grams/denier and most preferably from about 7 grams/denier to about 8.5 grams/denier. The percent elongation to break is preferably less than 25%, most preferably less than 20%. The filaments may have a hot air shrinkage at 350° C. from about 3 to 5% of the original length.

The filaments are typically extruded in bundles (yarns) havinging a denier from about 20 to about 500 and preferably are twisted to about 4–15 turns per inch. The twisted yarns are braided into sutures using conventional braid construction having a sheath and, optionally, a core according to, for example, U.S. Pat. No. 5,019,093. Alternatively, a spiral braid pattern may be used as described in U.S. Pat. Nos. 4,959,069 and 5,059,213. The braided suture may be stretched as before to increase length from about 9 to 28% over initial length. An absorbable or nonabsorbable coating can also be applied.

If desired to further enhance surface feel the stretched braid can be surface-etched and/or matte rolled. A needle is thereafter attached, the suture packaged and the product is sterilized.

The molecular weight of the filaments in the sterilized suture may be significantly less than that of the original filaments since processing and sterilization can break polymer chains.

The examples which follow are intended to illustrate certain preferred embodiments of the invention, and no limitation of the invention is implied.

EXAMPLE 1

Extrusion of PET Yarns

A PET yarn extrusion system employed in the invention is illustrated in FIG. 1. Bulk PET resin (type TTF 1006C, available from Shell Chemical Co.) having an intrinsic viscosity of 1.04 was dried overnight in an oven at 110–130° C. under a vacuum of less than 2 Torr. The oven was brought to atmospheric pressure with dry air. The dried resin was transferred to feed hopper 10 of the extrusion system and introduced into extruder barrel 20 which is 0.75 inches in diameter and 15 inches long via an extrusion screw (not shown). The extruder barrel contained three heating zones (or extrusion zones)—zones 1, 2 and 3. The heated and softened resin from the extruder was fed into a metering pump (melt pump) 25, and from melt pump 25 the extruded resin was fed into spin head 30.

Spin head 30 houses a spin pack comprising filtering media (screens) and a spinnerette containing from 16 to 35 holes (not shown) for forming the individual filaments of the yarn. The extruded filaments 50 exited the spinnerette through hot collar 40, and were then air-cooled until they solidified. The resulting yarn was then passed through a finish applicator 60, over two rotating godets 70 and 80, and was collected on precision winder 90 as the yarn exited the second godet 80. The denier of the yarn at this point was 354.

The operating parameters for the extrusion system are shown in Table 2.

TABLE 2

| Station | Units | Value |
| --- | --- | --- |
| Extrusion Screw | Rotations/Minute | 42 |
| Extrusion Zone 1 | Temperature ° C. | 320 |
| Extrusion Zone 2 | Temperature ° C. | 320 |
| Extrusion Zone 3 | Temperature ° C. | 320 |
| Melt Pump 25 | Temperature ° C. | 310 |
| Melt Pump Size | cc/Revolution | 0.584 |
| Melt Pump Rate | Rotations/Minute | 25.9 |
| Spin Pack Pressure | Pounds/ Sq. Inch | 2764 |
| Spinnerette | Number of Holes | 28 |
| Spinnerette Hole Diameter | Mils | 10 |
| Hot Collar 40 | Temperature ° C. | 250 |
| First Godet 70 | Temperature ° C. | Ambient |
| First Godet 70 | Surface Speed (fpm) | 1500 |
| Second Godet 80 | Temperature ° C. | Ambient |
| Second Godet 80 | Surface Speed (fpm) | 1507 |

EXAMPLE 2

Drawing of Yarn Extruded in Example 1

Figure 2:
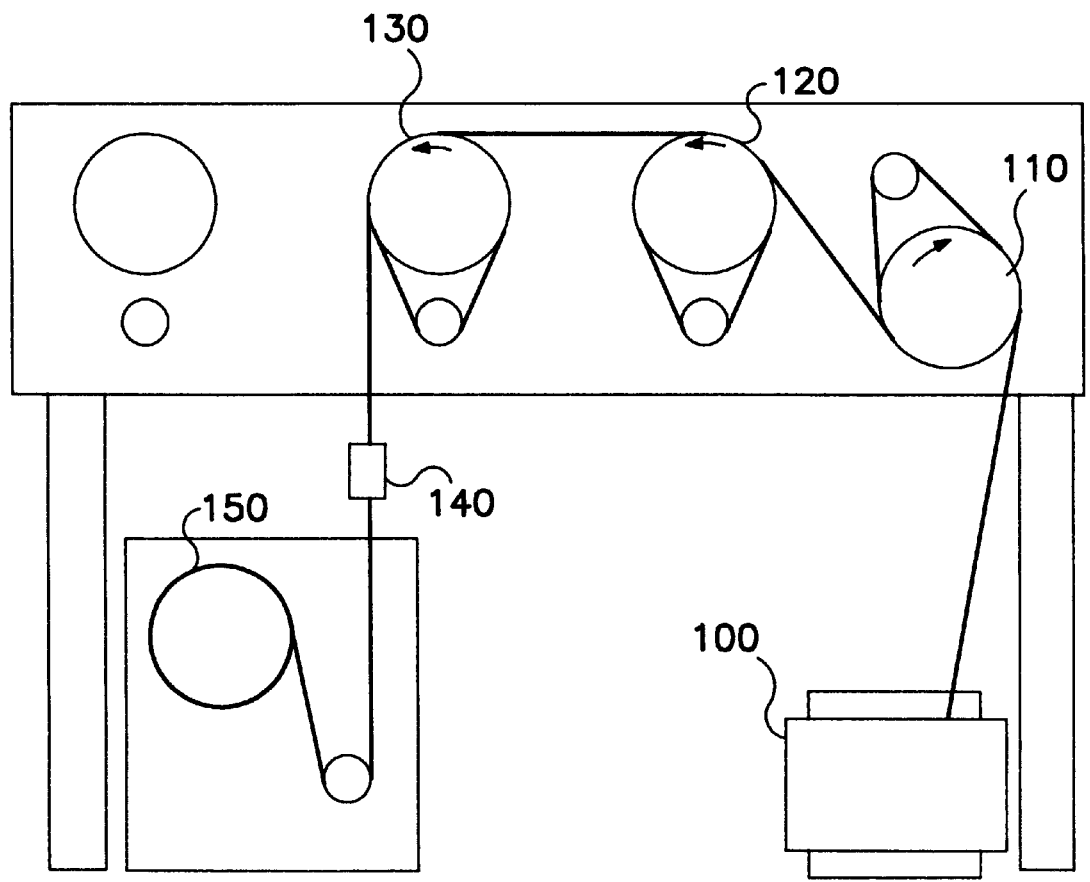
FIG. 2 is a plan view of a system for drawing polyester yarn.

After a six-day lag time the yarn extruded in Example 1 was drawn. Drawing was conducted by passing the extruded yarn 100 around multiple rotating rolls, as illustrated in FIG. 2. The drawing action was initiated by passing yarn 100 first over a roll (godet) 110 having a first, lower rotational speed and then over godets 120 and 130 having successively higher rotational speeds. Drawing occurred predominantly between godet 120 and godet 130 and was facilitated by heating the godets. The drawn yarn was entangled in air jet entangler 140 and then wound onto precision winder 150. The yarn drawing conditions are shown in

TABLE 3

| Item | Units | Value |
| --- | --- | --- |
| Godet 110 | Temperature ° C. | Ambient |
| Godet 110 | Surface Speed (fpm) | 500 |
| Godet 120 | Temperature ° C. | 77 |
| Godet 120 | Surface Speed (fpm) | 507 |
| Godet 130 | Temperature ° C. | 160 |
| Godet 130 | Surface Speed (fpm) | 2895 |

Properties of the drawn fiber were measured on an Instron Tensile Tester, Model 1130, equipped with cord and yarn clamps. The initial specimen length was 10 inches and the test was run at 10 inches of extension per minute. The results were as shown in Table 4.

TABLE 4

| Item | Value | Units |
| --- | --- | --- |
| Denier | 64.5 | — |
| Tenacity | 8.73 | g/denier |
| Breaking Elongation | 14.6 | percent |

EXAMPLE 3

Braided Polyester Sutures

The drawn yarn produced in Example 2 was formed into a suture as follows: Yarn samples were plied at 3 turns per inch and then braided on a New England Butt 8 carrier braider (not shown) at 38.6 picks per inch. The braid was then hot stretched in a tunnel between opposed matte surfaced godets numbered (1) and (2) under the conditions shown in Table 5. The braid was stretched 21%.

TABLE 5

| Item | Units | Value |
| --- | --- | --- |
| Godet 1 | Temperature ° C. | 200 |
| Godet 1 | Surface Speed (fpm) | 14 |
| Tunnel | Temperature ° C. | 231 |
| Godet 2 | Temperature ° C. | 200 |
| Godet 2 | Surface Speed (fpm) | 17 |

The stretched braid was softened by treatment in 3% NaOH aqueous solution maintained at 82.2° C. for 30 minutes. The softened braid was then washed and rinsed. The washed braid was then immersed in a solution of 5% silastic rubber and benzoyl peroxide as actives in a xylene solvent to coat the braid. The silastic rubber-coated braid was next cured in an oven at 170° C. and converted into a suture by attaching a needle, packaging and finally sterilizing with ethylene oxide. The properties of the suture were as in Table 6.

TABLE 6

| Property Measured | Value | Units |
| --- | --- | --- |
| Diameter | 0.315 | mm |
| Denier | 930 | |
| Tenacity[1] | 7.45 | g/denier |
| Breaking Elongation | 14.0 | percent |
| Knot Pull[2] | 2.93 | Kg |

[1]Tenacity was determined by a straight pull of a sample using a 10 inch gauge length and 10 inch per minute crosshead speed. "Cord and yarn" clamps were used for this purpose.
[2]Knot pull was determined by tying a sample in a "surgeon's knot" around a piece of rubber tubing and testing as in determining tenacity.

The suture had an excellent feel, did not exhibit "chattering" during use and provided reduced tendency to break during knot tying.

EXAMPLE 4

Extrusion of PET Yarn

Bulk PET, sold as Arnite A06 100 and available from DSM Engineering Plastics, having an intrinsic viscosity of 1.07 (tetrachloroethoxyphenol) was processed as described in Example 1 under the operating parameters shown in Table 7 as follows:

TABLE 7

| Station | Units | Value |
| --- | --- | --- |
| Extrusion Screw | Rotations/Minute | 42 |
| Extrusion Zone 1 | Temperature ° C. | 315 |
| Extrusion Zone 2 | Temperature ° C. | 315 |
| Extrusion Zone 3 | Temperature ° C. | 315 |
| Melt Pump 25 | Temperature ° C. | 289 |
| Melt Pump Size | cc/Revolution | 0.584 |
| Melt Pump Rate | Rotations/Minute | 24.9 |
| Spin Pack Pressure | Pounds/Sq. Inch | 3425 |
| Spinnerette | Number of Holes | 28 |
| Spinnerette Hole Diameter | Mils | 10 |
| Hot Collar 40 | Temperature ° C. | 250 |
| First Godet 70 | Temperature ° C. | Ambient |

TABLE 7-continued

| Station | Units | Value |
| --- | --- | --- |
| First Godet 76 | Surface Speed (fpm) | 1500 |
| Second Godet 80 | Temperature ° C. | Ambient |
| Second Godet 80 | Surface Speed (fpm) | 1507 |

Fiber was taken up on precision winder 90 as it exited second godet 80. The denier of the yarn at this point was 341.

EXAMPLE 5

Drawing of Extruded Yarn of Example 4

After a lag time of three (3) days, the extruded yarn of Example 4 was drawn as described in Example 2, using the drawing conditions shown in Table 8.

TABLE 8

| Item | Units | Value |
| --- | --- | --- |
| Godet 110 | Temperature ° C. | Ambient |
| Godet 110 | Surface Speed (fpm) | 500 |
| Godet 120 | Temperature ° C. | 77 |
| Godet 120 | Surface Speed (fpm) | 507 |
| Godet 130 | Temperature ° C. | 160 |
| Godet 130 | Surface Speed (fpm) | 2900 |

Drawn fiber was taken up on precision winder 150 as it exited godet 130. The properties of the drawn fiber are shown in Table 9.

TABLE 9

| Item | Value | Units |
| --- | --- | --- |
| Denier | 60.9 | — |
| Tenacity | 8.86 | g/denier |
| Breaking Elongation | 12.7 | percent |

EXAMPLE 6

Braided Polyester Sutures

The drawn yarn produced in Example 5 was converted to a suture as follows: Yarn samples were two plied at 3 turns per inch and then braided on a New England Butt 8 carrier braider. The braid was then hot stretched under the conditions shown in Table 10 to stretch the braid 33%.

TABLE 10

| Item | Units | Value |
| --- | --- | --- |
| Godet 1 | Temperature ° C. | Ambient |
| Godet 1 | Surface Speed (fpm) | 44.8 |
| Tunnel | Temperature ° C. | 254 |
| Godet 2 | Temperature ° C. | 23 |
| Godet 2 | Surface Speed (fpm) | 59.8 |

The stretched braids were softened and coated as described in Example 3. The properties of the finished braids are shown in Table 11.

TABLE 11

| Property Measured | Value | Units |
| --- | --- | --- |
| Diameter | 0.335 | mm |
| Denier | 1017 | — |
| Tenacity | 7.1 | g/denier |
| Breaking Elongation | 14.9 | percent |
| Knot pull | 3.2 | Kg |

Other variations and modifications of this invention will be obvious to those skilled in the art. This invention is not limited except as set forth in the following claims.

What is claimed is:

1. A braided polyester suture produced from a polymer having an intrinsic viscosity greater than about 0.95 and formed from yarn filament having (i) a tenacity of from about 7 to about 11 g/denier and (ii) a percent elongation to break of less than about 30 percent, said braided polyester suture having been surface etched to enhance feel.

2. A braided polyester suture produced from a polymer having an intrinsic viscosity greater than about 0.95 and formed from yarn filaments having (i) a tenacity of from about 7 to about 11 g/denier and (ii) a percent elongation to break of less than about 30 percent, said braided polyester suture having a matte finish to improve surface feel.

3. A braided polyester suture produced from a polymer having an intrinsic viscosity greater than about 0.95 and formed from yarn filaments having (i) a tenacity of from about 7 to about 11 g/denier and (ii) a percent elongation to break of less than about 30 percent, said braided polyester suture having a coating of silastic rubber.

4. The braided polyester suture of claims 1, 2 or 3 wherein the braided suture has the following construction:

| Braid Size | No. of Sleeve Yarns | Sleeve Yarns (denier/filament) | Core Yarn (denier/filament) | Picks/Inch |
| --- | --- | --- | --- | --- |
| 5 | 16 | 250/50 | 1000/200 | 52 |
| 2 | 16 | 140/68 | 840/408 | 57 |
| 1 | 12 | 140/68 | 630/306 | 52 |
| 0 | 12 | 100/34 | 300/102 | 42 |
| 2-0 | 8 | 140/68 | None | 39 |
| 3-0 | 8 | 80/16 | None | 39 |
| 4-0 | 4 | 70/34 | None | 39 |
|  | 4 | 40/8 |  |  |
| 5-0 | 8 | 30/20 | None | 33 |
| 6-0 | 4 | 30/20 | None | 32 |
|  | 4 | 20/10 |  |  |
| 7-0 | 3 | 20/10 | None | 67. |

5. The braided polyester suture of claim 4, wherein the yarn filaments have a tenacity of from about 7.5 to about 10.5 g/denier, a percent elongation to break of less than about 25 percent when produced from a polymer having an intrinsic viscosity greater than about 0.95 but no greater than about 1.1.

6. The braided polyester suture of claim 5, wherein the yarn filaments have a tenacity of from about 8 to about 10 g/denier and a percent elongation to break of less than about 20 percent.

* * * * *